United States Patent [19]

Becker et al.

[11] 4,355,186

[45] Oct. 19, 1982

[54] PROCESS FOR THE PREPARATION OF 4-PHENOXY-PHENOLS

[75] Inventors: Werner Becker, Frankfurt am Main; Klaus Dehmer, Kelkheim; Klaus Kaiser, Frankfurt am Main; Karl Rehn, Hofheim, all of Fed. Rep. of Germany

[73] Assignee: Hoechst Aktiengesellschaft, Frankfurt am Main, Fed. Rep. of Germany

[21] Appl. No.: 277,288

[22] Filed: Jun. 25, 1981

[30] Foreign Application Priority Data

Jun. 27, 1980 [DE] Fed. Rep. of Germany ....... 3024157

[51] Int. Cl.$^3$ .................. C07C 149/34; C07C 149/36; C07C 41/26
[52] U.S. Cl. ..................................... 568/52; 568/637; 568/638; 260/141
[58] Field of Search ............... 568/638, 629, 767, 637, 568/52; 260/141

[56] References Cited

FOREIGN PATENT DOCUMENTS 667229 7/1963 Canada ................................. 568/767
2648644 5/1978 Fed. Rep. of Germany ...... 568/638
391128 12/1973 U.S.S.R. ............................. 568/638

OTHER PUBLICATIONS

Hilgetag, Weygand/Hilgetag, Preparative Organic Chemistry, (1972), 581–583, 342–345.

*Primary Examiner*—Bernard Helfin
*Attorney, Agent, or Firm*—Curtis, Morris & Safford

[57] ABSTRACT

Substituted 4-phenoxy-phenols are prepared by adding the corresponding anilines in liquid or molten state together with aqueous sodium nitrite solution in equimolar amounts to excess HCl and introducing the diazonium chloride solution obtained into a boiling mixture of about half-concentrated $H_2SO_4$ and an aromatic hydrocarbon.

5 Claims, No Drawings

PROCESS FOR THE PREPARATION OF 4-PHENOXY-PHENOLS

The invention relates to a semi-continuous or fully continuous industrial process for the preparation of 4-phenoxy-phenols of the general formula I

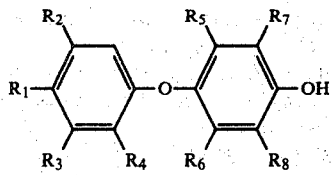

in which $R_1$ represents hydrogen, methylthio, cycloalkyl, aryl or halogen, $R_2$ and $R_3$ independently of one another each represents hydrogen, halogen or alkyl, $R_4$ represents hydrogen, alkyl, cycloalkyl or halogen, $R_5$, $R_6$ and $R_7$ independently of one another each represents hydrogen or alkyl and $R_8$ represents hydrogen and/or alkyl, by diazotizing the corresponding anilines of the general formula II

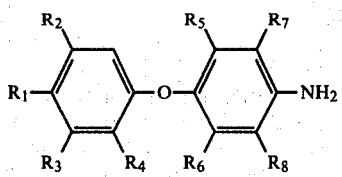

and subsequently decomposing the diazonium salts formed by boiling with sulfuric acid.

It is known to prepare phenols by diazotizing corresponding anilines and decomposing the diazonium salt solution formed by boiling (Ullmann V, 812; Houben-Weyl VI, 1c, 247; German Offenlegungsschrift No. 2,648,644). As a rule, however, either the yields or the space-time yields are unsatisfactory: in general, the solubility of the diazonium salts decreases in the order nitrate-chloride-bisulfate (compare, for example, Ullmann, 4th edition, volume 10, page 111, last paragraph). Preferably, the diazotization is therefore carried out in a solution containing nitric acid or hydrochloric acid, if it is desired to avoid difficulties due to solubility, in the diazotization stage. The diazonium nitrates are, however, unsuitable for the subsequent decomposition by boiling, since nitro compounds are formed from these to a frequently considerable extent (for example, Houben-Weyl, 4th edition, volume 6/1c, page 249). It is also known that, in the presence of halogen ions, an exchange of the diazonium group for halogen readily occurs, in particular in the case of relatively high halogen concentrations.

For these reasons, the relevant literature contains the technical teaching that "the diazotization for the so-called decomposition of diazo compounds by boiling on a preparative scale should not be carried out in hydrochloric acid, as is customary, but in sulfuric acid" (Ullmann, 4th edition, volume 10, pages 126/127).

However, the solubility of the anilines, and of the diazonium salts obtained from them, in sulfuric acid is particularly low (see above). At the customarily used temperatures of about 0°-20°, the initial formation of an aniline salt does not occur at all so that the diazotization (which proceeds via the stage of the aniline salt) does not take place. It is therefore necessary first to prepare a suspension of the aniline salt which is to be diazotized, in a separate stirred vessel and at an elevated temperature.

It has now been found, surprisingly, that the relatively good solubility of the chlorides of both the bases and their diazonium derivatives can be utilized for a diazotization without previously forming a suspension of the salt of the base, and for subsequently obtaining the corresponding phenol in a high space-time yield and purity, if this is carried out by the process according to the invention. This process comprises adding the liquid or molten aniline of the formula II and an approximately equimolar quantity of aqueous sodium nitrite solution at 0°-50° C., preferably 20°-30° C., simultaneously to an excess of aqueous hydrochloric acid, introducing the resulting diazonium chloride solution continuously into a mixture of approximately half-concentrated sulfuric acid and an aromatic hydrocarbon at the boiling point of the mixture thereof and simultaneously distilling off hydrochloric acid azeotropically.

About 10-20% strength by weight, preferably 13-20% strength by weight, hydrochloric acid is used for the diazotization, and the added $NaNO_2$ solution is advantageously of about 40% strength.

Expediently, the quantity of hydrochloric acid is such that, relative to the amine employed, it is in a molar ratio of 1 to 2-1 to 3. The reaction can be monitored by measuring the pH value and the redox value. The heat of reaction is removed partially via the vessel wall, but mainly via an external heat exchanger. The advantage of this process is that the customary previous formation of a suspension of the salt of the base before the addition of the sodium nitrite solution is dispensed with and, as a result, a favorable space-time yield is achieved. An additional enamelled stirred vessel for the previous formation of the suspension of the salt of the base is not required.

Surprisingly, it has been found that the presence of even very small amounts of nitrate ions, which are frequently present in varying concentration in industrial nitrite solutions, in the diazonium salt solution causes a reduction in the yield and a deterioration of the products of the formula I obtained by the process. In contrast to the known literature (for example Houben-Weyl, loc. cit.), the by-products formed here are not nitro compounds, but mono-nuclear and tri-nuclear phenols as the result of a disproportionation on the phenol ether bond. It is therefore important to employ nitrate-free sodium nitrite.

The decomposition of the diazonium salt solution by boiling is advantageously carried out in a two-stage cascade, consisting of two stirred vessels. A mixture of an aromatic hydrocarbon-preferably xylene or toluene, but benzene or chlorobenzene is also suitable-and of about 50-70% strength by weight sulfuric acid is here initially introduced, and the diazonium salt solution and hydrocarbon/sulfuric acid mixture are continuously metered in at temperatures in the range of the boiling point (110°-130°, preferably 115°-125°). To maintain the steady-state concentration, hydrochloric acid is distilled off azeotropically. The main quantity of the energy required for distillation is supplied in the first reactor via an external tubular heat exchanger. The reaction mixture is continuously withdrawn from the second reactor and is separated into product solution and sulfuric acid in a separator device. The hydrochloric acid and sulfuric acid are re-used after regeneration.

Under the conditions described, 90% of the diazonium salt solution were converted in the first reactor, and the remaining 10% were converted in the second reactor, at a mean total residence time of 2 to 5 hours. The main advantage of the continuous process is the high space-time yields. In two reactors of 2 m³ useful capacity each, up to 1 kmole/hour of diazonium salt solution can be decomposed by boiling. With a minimum outlay on operator effort and control engineering, the reaction product is steadily obtained in a high yield and constant quality.

The two acids can be re-used to an unlimited extent. It is only necessary to distil the additional water, originating from the nitrite solution and from the diazotization reaction, out of the hydrochloric acid, while the sulfuric acid is directly re-used after the proportion which has been discharged as sodium bisulfate has been replaced.

EXAMPLE I

(a) Diazotization 2,195 kg of 20% strength by weight hydrochloric acid are initially introduced into a 4 m³ enamelled stirred vessel which is interconnected to an enamelled condenser. At a temperature of 25° C. to 30° C., 1,205 kg of molten 2,4-dichloro-4'-amino-diphenyl ether and 834 kg of 40% strength by weight $NaNO_3$-free sodium nitrite solution in a molar ratio of 1 to 1 are simultaneously metered in within 5 hours, while stirring and circulating by means of a pump. The reaction is monitored by measuring the pH value and the redox value.

(b) Decomposition by boiling 536 kg/hour of diazonium chloride solution, 500 kg/hour of xylene and 1,290 kg/hour of 50% strength by weight sulfuric acid are metered simultaneously, while stirring and circulating by means of a pump, into a heatable 2.5 m³ enamelled stirred vessel which is fitted with a condenser and a downstream separator interconnected with a tubular heat exchanger. During this stage, such a quantity of hydrochloric acid is distilled off together with xylene that the reaction temperature of 118° C. is maintained. The reaction mixture is continuously transferred into a second reactor, where the reaction is completed, the remaining hydrochloric acid being distilled off together with xylene. The xylene which has been distilled off is recycled into the two reactors. The hydrochloric acid which has been separated off is reconcentrated to 20% by weight and is re-introduced into the diazotization.

The reaction mixture runs from the second reactor via an overflow into a separator, where the xylene phase is separated from the sulfuric acid. The sulfuric acid, if necessary after cooling, is freed from sodium bisulfate which has crystallized out, and is recycled to the decomposition by boiling, after the consumed proportion has been made up.

800 kg/hour of product solution in xylene are obtained. The content of 2,4-dichloro-4'-hydroxydiphenyl ether, determined by quantitative analysis by gas chromatography, is 17.2% by weight, which corresponds to a yield of 90% of theory.

EXAMPLE II

When 40% strength by weight sodium nitrite solution which additionally contains 3% by weight of sodium nitrate is employed in the process according to Example I, a yield of only 87% of theory of 2,4-dichloro-4'-hydroxydiphenyl ether is obtained. The missing 3% are found mainly in the form of disproportionated diphenyl ether derivatives, namely mono-nuclear and tri-nuclear phenols, and in the form of resins.

EXAMPLE III 230 g of 17.2% strength by weight hydrochloric acid (=1.08 mole) were initially introduced and 119.5 g of molten 2-chloro-4-bromo-4'-amino-diphenyl ether (=0.4 mole) and 71 g of 40% strength by weight sodium nitrite solution (=0.41 mole) were simultaneously added dropwise in the course of 45 minutes at 23°–28° C. After further stirring for 15 minutes, the clear solution was added dropwise at 120°–122° C. in the course of 90 minutes to a well-stirred mixture of 780 g of 65% strength by weight sulfuric acid and 410 g of xylene. During this addition, hydrochloric acid was continuously distilled off azeotropically. Stirring was continued for a further 30 minutes after the end of the addition.

After cooling to 30° C., the phases were separated, the phenol ethers formed were extracted from the xylene phase by means of sodium hydroxide solution, and the neutral by-products in the fully extracted xylene were determined.

By acidifying in the presence of xylene, the phenoxyphenols dissolved in the sodium hydroxide solution were transferred into the former and were analyzed.

When pure sodium nitrite was used, 2-chloro-4-bromo-4'-hydroxy-diphenyl ether was obtained in 88.6% yield and 97.64% purity, in addition to 6.3% of neutral by-products.

When the nitrite used contained 2.5% by weight of sodium nitrate, relative to sodium nitrite, the phenoxyphenol was formed only in 84.6% yield and 95.6% purity, in addition to 9.1% of neutral by-products and 0.6% each of mono-nuclear and tri-nuclear phenols.

We claim:

1. In process for the preparation of a 4-phenoxyphenol of the formula

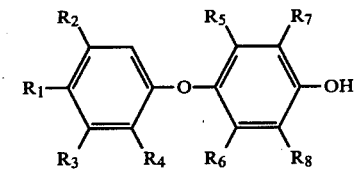

in which $R_1$ is hydrogen, methylthio, cycloalkyl, aryl or halogen, $R_2$ and $R_3$ independently of one another each is hydrogen, halogen or alkyl, $R_4$ is hydrogen, alkyl, cycloalkyl or halogen, $R_5$, $R_6$ and $R_7$ independently of one another each is hydrogen or alkyl and $R_8$ is hydrogen or alkyl, by diazotizing the corresponding aniline of the formula

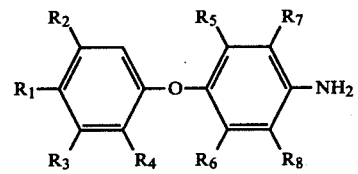

and subsequently decomposing the resulting diazonium salt or salts by boiling with sulfuric acid, the improvement which comprises simultaneously adding the aniline, in the liquid or molten state, and aqueous nitrate-free sodium nitrite solution in a molar ratio of about 1:1 at 0°–50° to an excess of aqueous hydrochloric acid of 10 to 20% strength and introducing the diazonium chloride solution obtained into a boiling mixture of approximately half-concentrated sulfuric acid of 50 to 70% strength and an aromatic hydrocarbon, hydrochloric acid being distilled off simultaneously.

2. A process as claimed in claim 1, wherein hydrochloric acid together with xylene or toluene is distilled off azeotropically in the stage of decomposition by boiling, in order to maintain the steady-state concentration.

3. A process as claimed in claim 2, wherein the hydrochloric acid is completely recycled into the process and the sulfuric acid is recycled to the extent that it has not been consumed by the formation of sodium bisulfate.

4. A process as claimed in claim 1, wherein the aromatic hydrocarbon is benzene, toluene, xylene or chlorobenzene.

5. A process as claimed in claim 1, wherein the hydrochloric acid is of 13 to 20% strength.

* * * * *